(12) United States Patent
Baker et al.

(10) Patent No.: US 10,363,416 B2
(45) Date of Patent: Jul. 30, 2019

(54) ELECTROSTIMULATION TO INCREASE PERFUSION

(71) Applicant: HILL-ROM SERVICES, INC., Batesville, IN (US)

(72) Inventors: Steven D. Baker, Beaverton, OR (US); Timothy A. Lane, Shrewsbury, MA (US)

(73) Assignee: Hill-Rom Services, Inc., Batesville, IN (US)

( * ) Notice: Subject to any disclaimer, the term of this patent is extended or adjusted under 35 U.S.C. 154(b) by 92 days.

(21) Appl. No.: 15/811,743

(22) Filed: Nov. 14, 2017

(65) Prior Publication Data

US 2018/0140837 A1    May 24, 2018

Related U.S. Application Data

(60) Provisional application No. 62/425,649, filed on Nov. 23, 2016.

(51) Int. Cl.
| | |
|---|---|
| *A61N 1/36* | (2006.01) |
| *A61N 1/04* | (2006.01) |
| *A61B 5/00* | (2006.01) |
| *A61B 5/11* | (2006.01) |
| *A61B 5/026* | (2006.01) |

(52) U.S. Cl.
CPC .......... *A61N 1/36031* (2017.08); *A61B 5/026* (2013.01); *A61B 5/11* (2013.01); *A61B 5/4836* (2013.01); *A61B 5/6891* (2013.01); *A61N 1/0492* (2013.01); *A61N 1/36034* (2017.08)

(58) Field of Classification Search
CPC ......... A61B 5/026; A61B 5/11; A61B 5/4836; A61B 5/6891; A61N 1/0492; A61N 1/36031
See application file for complete search history.

(56) References Cited

U.S. PATENT DOCUMENTS

| | | | |
|---|---|---|---|
| 6,010,455 A | 1/2000 | Barnett et al. | |
| 6,248,066 B1 | 6/2001 | Barnett et al. | |
| 6,488,623 B1 | 12/2002 | Ozarowski et al. | |
| 6,631,294 B2 | 10/2003 | Andino et al. | |
| 6,907,294 B2 | 6/2005 | Andino et al. | |
| 7,395,112 B2 | 7/2008 | Keisari et al. | |
| 7,742,829 B2 | 6/2010 | Rainey et al. | |
| 8,738,143 B2 | 5/2014 | Tucker et al. | |
| 8,774,945 B2 | 7/2014 | Freeman | |
| 8,781,577 B2 | 7/2014 | Freeman | |
| 9,180,287 B2 | 11/2015 | Gonzalez et al. | |
| 9,242,115 B2 | 1/2016 | Freeman | |
| 9,364,680 B2 | 6/2016 | Freeman | |

(Continued)

FOREIGN PATENT DOCUMENTS

WO    2007088348 A2    8/2007

OTHER PUBLICATIONS

"The effect of ischaemia on nerve conduction in the carpel tunnel syndrome" Pamela M. Fullerton; Neurol. Neurosurg. Psychiat., 1963, 26, 385; 1 page available from internet.

(Continued)

*Primary Examiner* — George Manuel
(74) *Attorney, Agent, or Firm* — Barnes & Thornburg LLP (57) ABSTRACT

Devices, systems, and methods are disclosed for encouraging perfusion by electrostimulation.

20 Claims, 6 Drawing Sheets

(56) References Cited

U.S. PATENT DOCUMENTS

| | | |
|---|---|---|
| 9,421,331 B2 | 8/2016 | Linton et al. |
| 9,579,244 B2 | 2/2017 | Linton et al. |
| 9,839,576 B2 | 12/2017 | Freeman |
| 9,867,977 B2 | 1/2018 | Sumners et al. |
| 2003/0144723 A1 | 7/2003 | Andino et al. |
| 2015/0032184 A1 | 1/2015 | Muccio |
| 2016/0029960 A1* | 2/2016 | Toth .................. A61B 18/1492 600/301 |

OTHER PUBLICATIONS

"The effect of ischaemia on the excitability of human sensory nerve" K.N. Seneviratne; J. Neurol. Neurosurg. Psychiat., 1968, 31, 338-347; 1 page available from internet.

"Use of somatosensory evokes potentials to detect peripheral ischemia and potential injury resulting from positioning of the surgical patent: case reports and discussion" Stanley C. Jones; The Spine Journal, May-Jun. 2004, vol. 4, Issue 3, pp. 360-362; 1 page available from internet.

"Deep Tissue Afferents, but not Cutaneous Afferents, Mediate Transcutaneous Electrical Nerve Stimulation-Induced Antihyperalgesia" Rajan Radhakrishnan; The Journal of Pain, vol. 6, Issue 10, Oct. 2005, pp. 673-680; 1 page available from internet.

"Current distribution under electrodes in relations to simulation current and skin blood flow: are modern electrodes really providing the current distribution during stimulation we believe they are?" J. Petrofsky; Journal of medical Engineering & Technology, vol. 30, 2006 Issue 6; 1 page (Abstract only).

"An effective method for skin blood flow measurement using local heat combined with electrical stimulation" A.-M. R. Almalty; Journal of Medical Engineering & Technology, vol. 33, 2009 Issue 8; 1 page (Abstract only).

"Electrical stimulation to accelerate wound healing" Gaurav Thakral, MD; Diabetic Foot & Ankle. 2013; 4: doi: 10.3402/dfa.v4i0.22801; 10 pages.

* cited by examiner

ELECTROSTIMULATION TO INCREASE PERFUSION

The present disclosure claims the benefit, under 35 U.S.C. § 119(e), of U.S. Provisional Application No. 62/425,649, filed Nov. 23, 2016, and which is hereby incorporated by reference herein in its entirety.

BACKGROUND

The present disclosure relates to devices, systems, and methods for encouraging perfusion. More specifically, present disclosure relates to devices, systems, and methods for encouraging perfusion in specific areas of a patient's body.

Poor blood flow to areas of a patient's body can create discomfort and can present hazards to the patient. Patients with limited mobility are particularly susceptible to local blood flow restrictions and their complications. Routine movement and/or hygiene practices can reduce discomfort and hazards resultant from such blood flow restrictions, but at times can fail to abate more lasting and/or serious problems associated therewith.

SUMMARY

The present application discloses one or more of the features recited in the appended claims and/or the following features which, alone or in any combination, may comprise patentable subject matter:

According to an aspect of the present disclosure, an electrostimulation system for encouraging perfusion in a patient's body may include a number of first stimulation pods providing a first polarity, each first stimulation pod engaging the patient's body, a number of second stimulation pods providing a second polarity, each second stimulation pod engaging the patient's body and being arranged with proximity to the first stimulation pods to create a directed electric field to encourage perfusion in nearby areas of the patient's body, and a controller connected with each of the first and second stimulation pods to communicate at least one stimulation signal to produce the first and second polarities, respectively.

In some embodiments, the system may include at least one sensor in communication with the controller. In some embodiments, the sensor may be adapted to indicate a measured perfusion level within the patient's body.

In some embodiments, the controller may be configured to determine whether the measured perfusion level meets a threshold perfusion level. In some embodiments, the controller may be configured to determine updated parameters for at least one of the first and second stimulation pods in response to determination that the measured perfusion level does not meet the threshold perfusion level. In some embodiments, the updated parameters may include change in a stimulus value of at least one of amplitude, duty cycle, modulation, and pulse frequency.

In some embodiments, the controller may be configured to determine the measured perfusion level by sending a reference signal through the patient's body to produce at least one response, detecting the at least one response produced by the reference signal, and evaluating the at least one response to determine the measured perfusion level. In some embodiments, the response may include an indication of reduced blood flow within a localized area of the patient's body. In some embodiments, the response may include change of the reference signal passed through the patient's body.

In some embodiments, the response may include localized motion of the patient's body and the sensor may include a micro-motion sensor for detecting the motion of the patient's body.

In some embodiments, the controller may be configured to determine a location of low perfusion of the patient's body based on the measured perfusion level. In some embodiments, the controller may be configured to determine a target direction of the directed electric field required to pass through the location of low perfusion and to adjust the at least one stimulation signal to achieve the directed electric field having the target direction. In some embodiments, the controller may be configured to determine that the target direction of the directed electric field required to pass through the location is beyond a capacity of the system according to current arrangement of first and second stimulation pods and to determine an adjusted arrangement of first and second stimulation pods to pass the directed electric field through the location. In some embodiments, the controller may output the adjusted arrangement of first and second stimulation pods onto a display for communication to a user.

According to another aspect of the present disclosure, a patient support system with electrostimulation for encouraging perfusion in a patient's body may include a support surface including number of first stimulation pods arranged to engage a body of a patient occupying the support surface, each first stimulation pod having a first polarity, and a number of second stimulation pods providing a second polarity, each second stimulation pod engaging the patient's body and being arranged with proximity to the first stimulation pods to create a directed electric field to encourage perfusion in nearby areas of the patient's body.

In some embodiments, the patient support may include a controller connected with each of the first and second stimulation pods to communicate at least one stimulation signal to produce the first and second polarities, respectively.

In some embodiments, the patient support system may include at least one sensor in communication with the controller, the sensor being adapted to indicate a measured perfusion level within the patient's body.

In some embodiments, the controller may be configured to determine a location of low perfusion of the patient's body based on the measured perfusion level. In some embodiments, the controller may be configured to determine a target direction of the directed electric field required to pass through the location of low perfusion and to adjust the at least stimulation signal to achieve the directed electric field to have the target direction.

In some embodiments, the controller may be configured to determine that the target direction of the directed electric field required to pass through the location is beyond a capacity of the system according to current arrangement of first and second stimulation pods and to determine an adjusted arrangement of first and second stimulation pods to pass the directed electric field through the location. In some embodiments, the controller may output the adjusted arrangement of first and second stimulation pods onto a display for communication to a user.

According to another aspect of the present disclosure, a pod for delivering therapy to a patient may include a stimulation terminal, a conductive body, the conductive body having a relief area to distribute contact forces.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Localized regions of a patient's body which receive less than desirable blood flow can produce pain, discomfort, and/or deterioration. Continued exposure to low blood circulation rates at localized areas can result in ulcers and/or other ailments which can be difficult to alleviate. For example, patients with limited mobility may develop pressure ulcers (bed sores) in part due to low blood flow rates around areas of the body receiving contact pressure for significant periods of time. In the case of pressure sores, prevention can be the preferred approach. After such sores have formed, even regular treatment (e.g., bed turns, bedding changes, etc.) can fail to eliminate the resultant pain and/or discomfort. Maintaining healthy blood flow, or perfusion, can combat and relieve the negative effects of such localized ischemia. Moreover, proper blood flow can assist recovery from various kinds of existing wounds.

Electrostimulation can encourage blood flow in a patient's body. Tissue can recover more quickly and completely with electrostimulation treatment. However, electrostimulation performed at the surface may not reach and/or effectively treat tissue below the surface (e.g., deep tissue).

Figure 1:
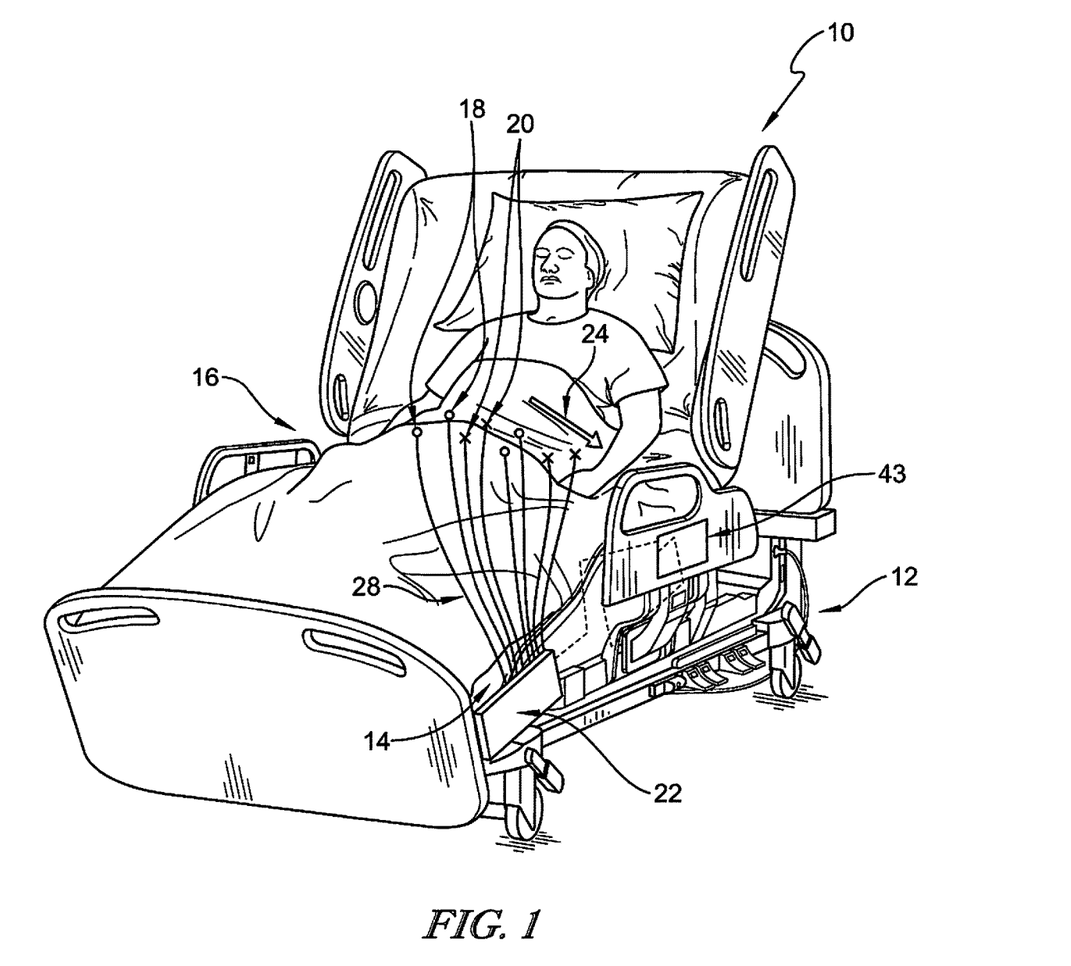
FIG. 1 is a perspective view of a patient bed including an electrostimulation system for encouraging perfusion (blood flow) in targeted areas within the patient's body showing that the electrostimulation system includes a number of pods engaging the patient's body and connected with a controller to generate a directed electric field.

In the illustrative embodiment shown in FIG. 1, a patient occupies a patient bed 10. The patient bed 10 illustratively includes a frame 12 that supports a support surface, or mattress, 14 above the floor. The patient bed 10 illustratively includes an electrostimulation system 16 for encouraging perfusion in the patient's body.

As shown in FIG. 1, the electrostimulation system 16 illustratively includes a number of stimulation pods 18, 20 engaged with the patient's body and connected with a controller 22 to receive electrical power. The pods 18, 20 illustratively include first pods 18 individually in communication with the controller 22 to have a first electric polarity or phase (e.g., negative polarity or 180-degree phase in some embodiments) and second pods 20 individually in communication with the controller 22 to have a second electric polarity or phase (e.g., positive polarity or 0-degree phase in some embodiments). In the illustrative embodiment, the first pods 18 are engaged with the anterior side of the patient's mid-section, while the second pods 20 are engaged with the patient's posterior side. The first and second pods 18, 20 are illustratively arranged with proximity to each other to create a directed electrical field 24 through the patient's body to stimulate blood flow. In one non-limiting example, for illustration purposes, the proximity of the pods 18, 20 to each other may be on the order of less than one inch to several feet. In some embodiments, phases other than 0 and 180 degrees can be applied. Generally, the term polarity can indicate polarity and/or phase.

Figure 2:
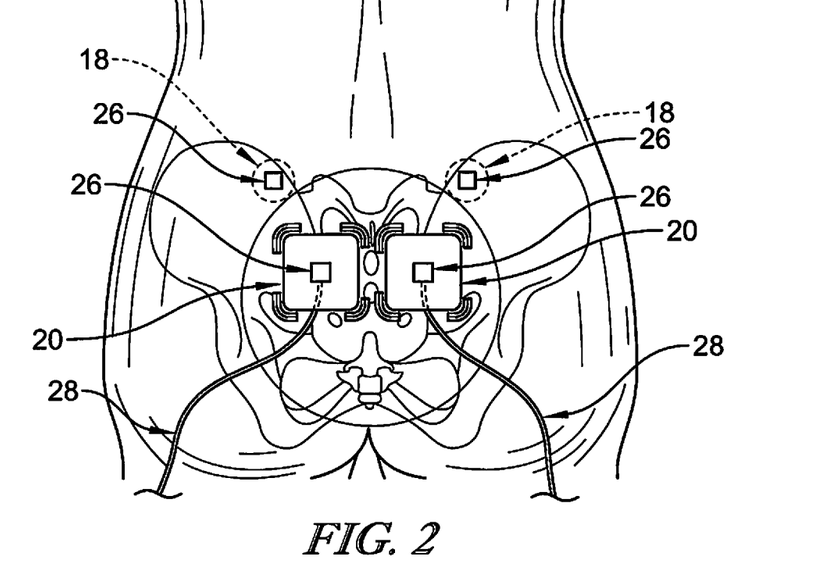
FIG. 2 is a rear view of the patient's body, near the pelvis, having several pods of the electrostimulation system of FIG. 1 applied to the patient's body showing that a pair of pods (square, solid line) are attached to the patient's back side near the sacrum and another pair of pods (circular, broken line) are attached to the patient's front side near the abdomen.

As shown in FIG. 2, the patient's lower back is shown from the rear with pods 18, 20 attached near the patient's mid-section on either side of the sagittal plane. A pair of pods 18 are illustratively attached to the patient's anterior side near the abdomen (shown in broken line to indicate the anterior side) and a pair of pods 20 are illustratively attached to the patient posterior side near the sacrum. The pods 18, 20 are illustratively embodied as contact pads applied directly to the patient's skin. Each pod 18, 20 illustratively includes a stimulation terminal 26, embodied as an electrode, that is electrically connected with the controller 22 by a wire 28. In some embodiments, the pods 18, 20 and/or wire 28 may include circuitry for configuring electrical signals communicated with the controller 22. Particular embodiments of the pods 18, 20 are discussed in additional detail below.

Figure 3:
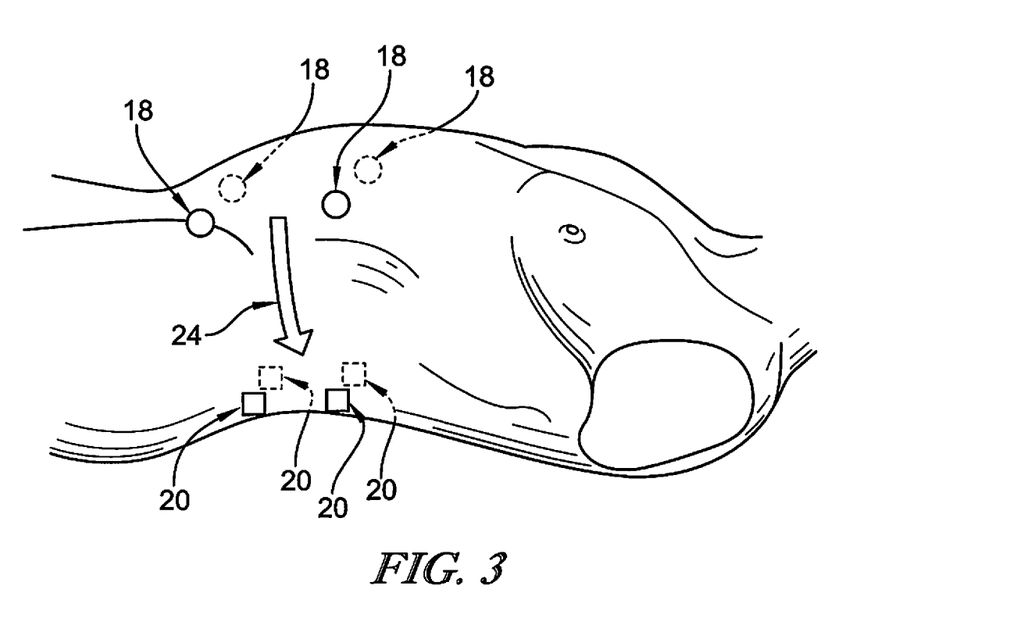
FIG. 3 is a side view of the electrostimulation system of FIGS. 1 and 2 applied to a patient's body lying in the supine position to show that four pods are attached to the patient's front side near the abdomen (circular) and four pods are attached to the patient's back side near the sacrum (square) such that the pods interact with each other to create a directed electric field through the patient's body as indicated by the arrow.

As shown in FIG. 3, the pods 18, 20 are shown attached to the patient while in the supine position. Four pods 18 are illustratively attached near the patient's abdomen with two on either side of the sagittal plane and four pods 20 are attached near the patient's sacrum with two on either side of the sagittal plane. The pods 18, 20 collectively generate the directed electrical field 24 based on the electrical signals from the controller 22.

Figure 4:
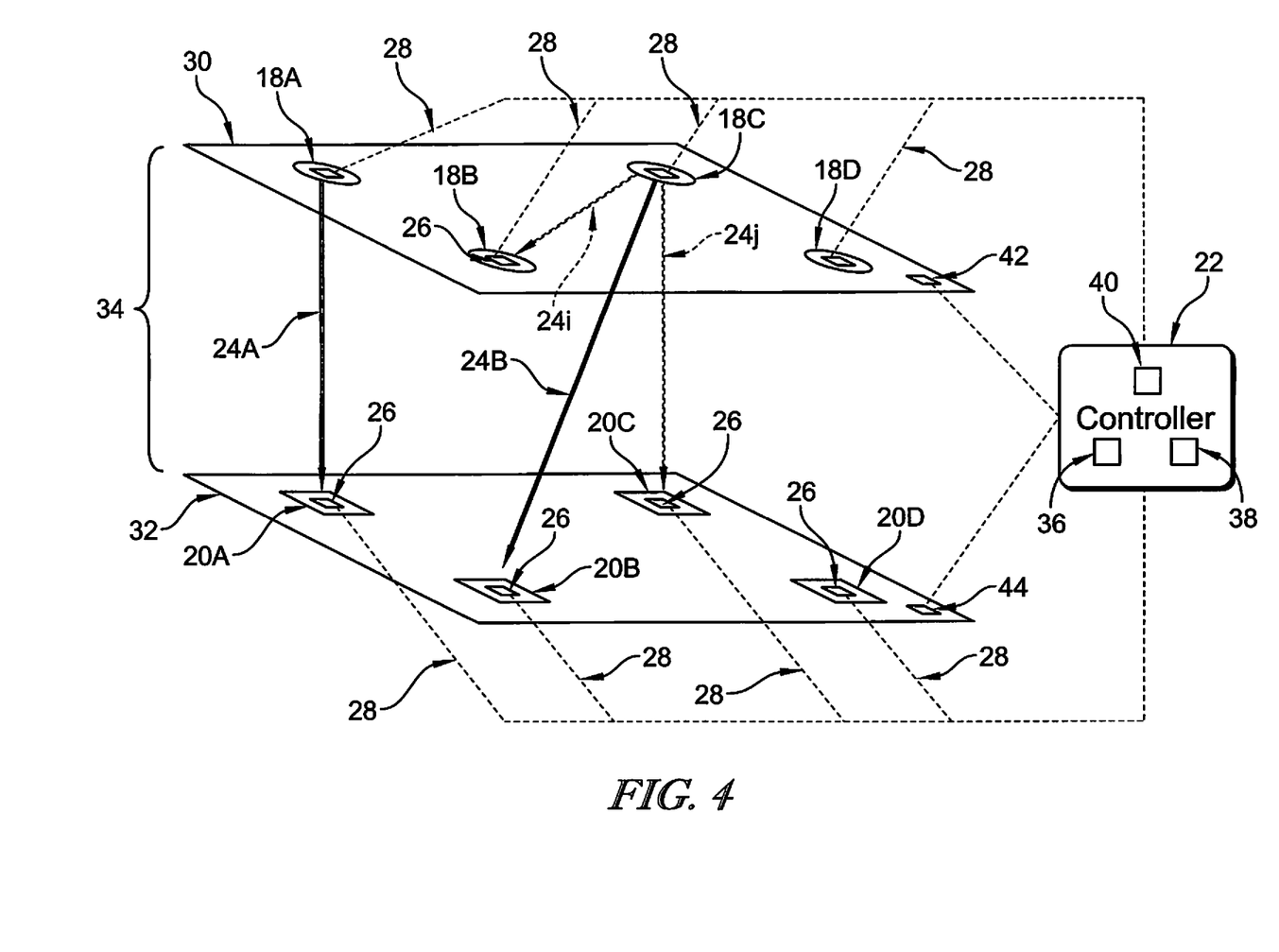
FIG. 4 is a diagrammatic view of the electrostimulation system of FIGS. 1-3 showing a number of (upper) pods engaged with a first region of a patient's body and a number of (lower) pods engaged with a second portion of the patient's body, the patient body being located between the first and second regions, and showing that the controller generates the directed electric field through the patient's body based on the collective electric influence of the pods, and showing that the electrostimulation system includes a sensor for detecting the amount of blood flow in areas of the patient's body and that the controller adjusts the direction of the directed electrical field based on information from the sensor.

As shown diagrammatically in FIG. 4, the pods 18, 20 are arranged to form a field network to create the directed electrical field 24A, 24B. The pods 18A-18D are engaged with a first surface region 30 of the patient's body and the pods 20A-20D are engaged with a second surface region 32 of the patient's body. The space 34 between the surface regions 30, 32 illustratively represents the thickness of the patient's body. The controller 22 communicates signals with the pods 18, 20 to generate electrical polarities in each pod 18, 20 to create the directed electric field 24.

As shown in FIG. 4, by non-limiting example, the directed electric field 24A is created by generating a negative voltage in pod 18A and a positive voltage in pod 20A, while the other pods 18B-18D, 20B-20D are set to zero voltage. The resultant directed electric field 24A is illustratively formed generally directly between the pods 18A, 20A. In another non-limiting example, generating negative voltages in pods 18B and 20C and a positive voltage in pod 18C, the directed electrical field 24B is created from the net electrical effects (the vector 24i from pod 18C to pod 18B added to the vector 24j from 18C to 20C). The directed electrical field 24 can thus be controlled for direction to pass through target locations of the patient's body by the combined electrical field effect of the pods 18, 20. As illustrated in this example, there is no requirement that each of pods 18 have the same polarity, nor is there a requirement that each of pods 20 have the same polarity and any relative phase/polarity may be generated between any sets of individual pods.

As mentioned above, the controller 22 is illustratively connected to the pods 18, 20 to generate their respective voltages. The controller 22 illustratively includes a processor 36 that executes instructions, a memory device 38 that stores instructions for execution on the processor 36, and power circuitry 40 for providing the electrical signals as directed by the processor 36 to generate the respective voltages in the pods 18, 20.

In the illustrative embodiment, the controller 22 applies direct current (DC) voltages to the pods 18, 20. In some embodiments, the controller 22 may apply one or more of DC, alternating current (AC), high-voltage pulse current (HVPC), low-intensity direct current (LIDC), and/or any other suitable type of electricity form and/or waveform to the pods 18, 20 and may apply different forms of stimulus to different pods 18A-18D, 20A-20D and/or at different times. In some embodiments, the pods 18, 20 may be configured to provide poles to create a directed magnetic field, for example but without limitation, having pods 18, 20 forming magnetic antennas, such as form from a loop of wire through which current is passed.

As shown in FIG. 4, the electrostimulation system 16 includes a sensor 42 in communication with the controller 22. The sensor 42 is illustratively adapted to detect perfusion level(s) within the patient's body and to communicate a signal to the controller 22 indicating the perfusion levels. The controller 22 illustratively determines an area of low blood flow by comparing the indicated perfusion levels to threshold levels illustratively stored by the controller 22.

As shown in FIG. 4, the electrostimulation system 16 illustratively includes a transmitter 44 for generating a reference signal for passage through the patient's body. The sensor 42 illustratively receives the reference signal from the transmitter 44 and communicates a signal indicating the received reference signal to the controller 22. The controller 22 illustratively analyzes the indication of the received reference signal to determine perfusion levels within the patient's body. In the illustrative embodiment, the controller 22 determines perfusion levels as outputs of at least one algorithm stored in the memory device 38, but in some embodiments may include any of a lookup table, comparison of the received references signal to the references signal sent from the transmitter 44, and/or any other suitable methods for determining threshold blood flow levels. In some embodiments, patient specific criteria may be inputs to the algorithm for determining customized thresholds.

In some embodiments, the sensor 42 may be embodied as a micro-motion sensor adapted to detect motion of the patient's body in response to a stimulus. For example but without limitation, the stimulus may include the stimulation signals, additional and/or different signals from the controller 22 to any of the pods 18, 20, and/or signals to the transmitter 44. In some embodiments, the sensor 42 may detect the electrical field parameters generated by the pods 18, 20 and may provide an indication of the detected electrical field parameters to the controller 22. The controller 22 may determine an area of low blood flow by comparing the indication of the electrical field parameter to predetermined electric field parameters stored with the memory device 38 as corresponding to the stimulation signals provided from the controller 22 to the pods 18, 20. The predetermined electrical field parameters may be outputs of an algorithm that describe the expected electrical field parameters when the electrical fields are passed through areas of the patient's body having sufficient blood flow. In the illustrative embodiment, a single sensor 42 and single transmitter 44 are shown, but in some embodiment any suitable number and/or arrangement of sensors 42 and/or transmitters 44 (including none) may be used. Accordingly, the electrostimulation system 16 can identify areas of low blood flow as target areas.

Figure 5:
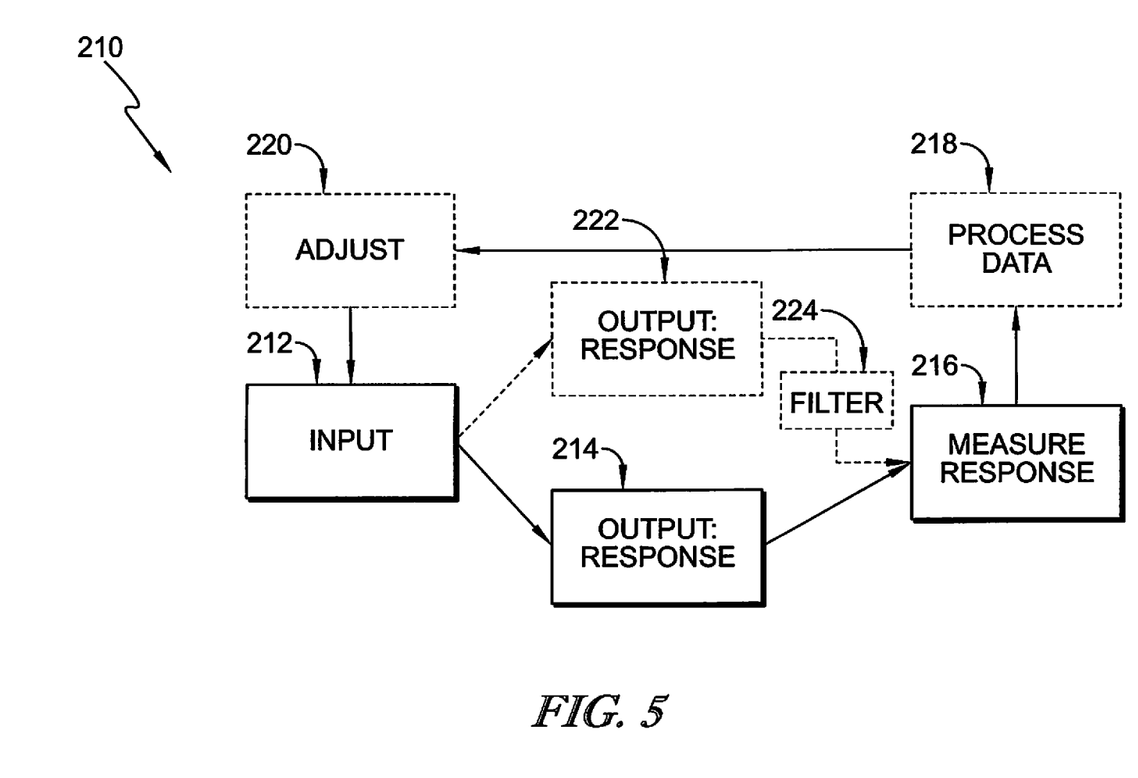
FIG. 5 is a process flow diagram of an operation of the electrostimulation system of FIGS. 1-4 showing that the electrostimulation system provides an input signal to the patient's body and measures the response from the patient's body to determine the blood flow in a local area of the patient's body, and showing that the system can optionally process and adjust operation.

As shown in FIG. 5, an illustrative process flow diagram depicts an operation 210 of the electrostimulation system 16. As indicated at block 212, the electrostimulation system 16 illustratively provides an input to the patient's body. In the illustrative embodiment, the input is the reference signal. In some embodiments, the input may include any suitable type of input, for example but without limitation, electrical, magnetic (e.g., diagnostic, imaging), chemical (e.g., marker, medicinal), and/or physical (e.g., pressure examination). The process proceeds to block 214.

As shown in FIG. 5, at block 214, the electrostimulation system 16 illustratively detects an output as a response to the input. In the illustrative embodiment, the output is embodied as change (e.g., deterioration, alteration) of the reference signal passed through the patient's body as detected by the sensor 42. In some embodiments, the output may include any of change in the electrical field parameters, motion of patient's body as mentioned above, and/or other suitable output/response mechanisms (electrical, magnetic, chemical/biological, and/or physical). The process proceeds to block 216.

As shown in FIG. 5, at block 216, the electrostimulation system 16 illustratively measures the response indicated by the output. In the illustrative embodiment, the controller 22 evaluates the output as the received reference signal to determine the perfusion levels within the patient's body by at least one algorithm. In some embodiments, the electrostimulation system 16 may measure the response by any of algorithm, lookup table, comparison to the transmitted input, and/or other suitable method. In some embodiments, the operation 210 may return to block 212.

As shown in FIG. 5, the operation 210 may optionally proceed to block 218 to process the information evaluated at block 216 (optionally indicated in broken line). In the illustrative embodiment, the electrostimulation system 16 optionally processes the determined perfusion levels to determine whether a response of the system 16 is desired. The controller 22 illustratively determines whether the determined profusion levels meet a threshold perfusion level. If the controller 22 determines that the threshold perfusion level is met, the electrostimulation system 16 illustratively continues current operations, and may illustratively return to block 212. If the controller 22 determines that the thresholds perfusion level is not met, the operation 210 illustratively determines a target direction of the area of low perfusion levels and proceeds to block 220 to adjust the current operation of the electrostimulation system 16. In some embodiments, in response to the perfusion thresholds levels being unmet, the controller 22 may determine target electrical field parameters, for example but without limitation direction, voltage levels, current levels, modulation, electricity, and/or waveform type and parameters, etc.

As shown in FIG. 5, the electrostimulation system 16 can optionally adjust the current operation as indicated at block 220. In the illustrative embodiment, the controller 22 adjusts the direction of the directed electrical field 24 to the target direction to pass through the area of low perfusion. In some embodiments, the controller 22 may adjust current electrical field parameters to provide updated and/or targeted stimulation to an area of low perfusion, for example but without limitation, the controller 22 may adjust the magnitude of the voltage differentials of the pods 18, 20 with or without changing the current direction of the directed electrical field 24. The operation 210 can return to block 212 from block 220. In the illustrative embodiment, changes to the current electrical field are embodied as collective changes to the operation of the pods 18, 20.

As shown in FIG. 5, the operation 210 may include an output responsive to input from block 212 as indicated at block 222. The output from block 222 illustratively passes through a filter module as indicated at block 224. The filter module indicated at block 224 is illustratively adapted to filter certain patient responses. The output from block 222 may optionally be provided in addition to (in parallel with) output from block 214 or in place of output from block 214. In some embodiments, any number of output responses may be generated and/or evaluated. The operation 210 may include such practicalities as numbing the patient's skin and directly measuring current passed therethrough, and/or locating and implementing a measurement location on the patient's body where the measured response is accurate. In configurations that numb the patient skin and/or use an analgesic, this activity can considered a bio-physiological filter as secondary analgesics may be used to direct electrical flow and/or isolate deep nerves.

Returning briefly to FIG. 1, the patient bed 10 illustratively includes a display screen 43 in communication with the controller 22. At block 218 in FIG. 5, the controller 22 can illustratively determine that the target direction (and/or target electrical field parameters) is beyond the capacity of the pods 18, 20 as currently arranged. If the controller 22 determines that target direction (and/or target electrical field parameters) is beyond the capacity of the pods 18, 20 as currently arranged, the controller 22 illustratively determines at least one adjusted arrangement of pods 18, 20 which brings the target direction (and/or target electrical field parameters) within the capacity of the pods 18, 20. The controller 22 illustratively communicates with the display screen 43 to display the adjusted arrangement of the pods 18, 20 for communication with a user. In the illustrative embodiment, the adjusted arrangement of the pods 18, 20 is displayed as a pictorial arrangement, but in some embodiments may include written instructions and/or step by step pictures and/or instructions for communication with the user.

Figure 6:
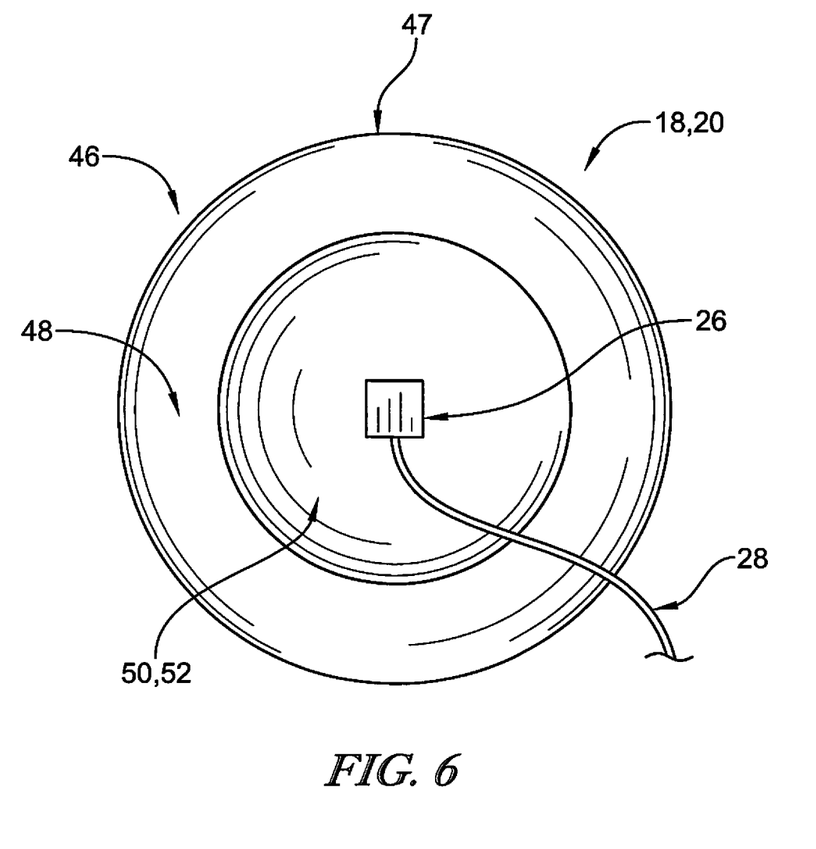
FIG. 6 is a top view of an illustrative embodiment of a pod of the electrostimulation system of FIGS. 1-4 showing that the pod includes a body having a contact area and a relief area, the relief area arranged within the contact area and having an opening defined therein, and a stimulator arranged within the relief area for providing electric polarity for conductance through the body.

As shown in FIG. 6, an illustrative embodiment of the pods 18, 20 is shown. Each pod 18, 20 illustratively includes a body 46 including a contact area 48 and a relief area 50 arranged within the contact area 48. The stimulation terminal 26 is illustratively arranged within the relief area 50 and the body 46 conducts the directed electrical field therethrough. The body 46 is illustratively formed as a circular disc and includes a conductive gel 45 contained within a deformable casing 47, but in some embodiments may have any suitable shape and/or form for conductive engagement with the patient's body. The body 46 engages the patient's body, illustratively by direct adhesion to the skin, such that the casing 47 is in contact with the patient's skin. Adhesion to the skin is illustratively provided by conductive adhesive applied to the casing 47. The conductive gel 45 and casing 47 provides additional resilient pressure relief to distribute contact forces and relieve load concentration.

Figure 7:
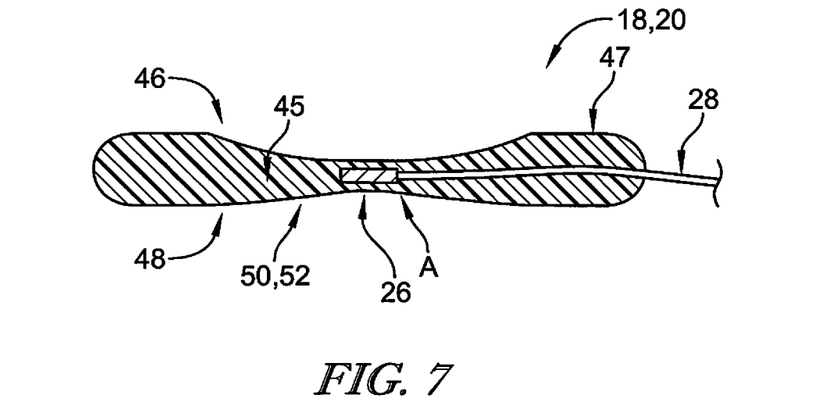
FIG. 7 is a side view of the pod of FIG. 8 showing that the contact area has a thickness, and the relief area has a transition thickness that forms a concave depression to relieve loading to the patient's body.

As shown in FIG. 7, the relief area 50 illustratively has a tapered thickness to form a depression 52. The stimulation terminal 26 is arranged within the depression 52. The taper of the relief area 50 reduces loading to the area A at which the pod 18, 20 is applied and distributes forces to surrounding areas. This provides a low loading point at the engagement of the pod 18, 20 with the patient's body. Low loading can provide comfort particularly to sensitive areas, for example, where the pod 18, 20 may be applied directly to a wound area.

Figure 8:
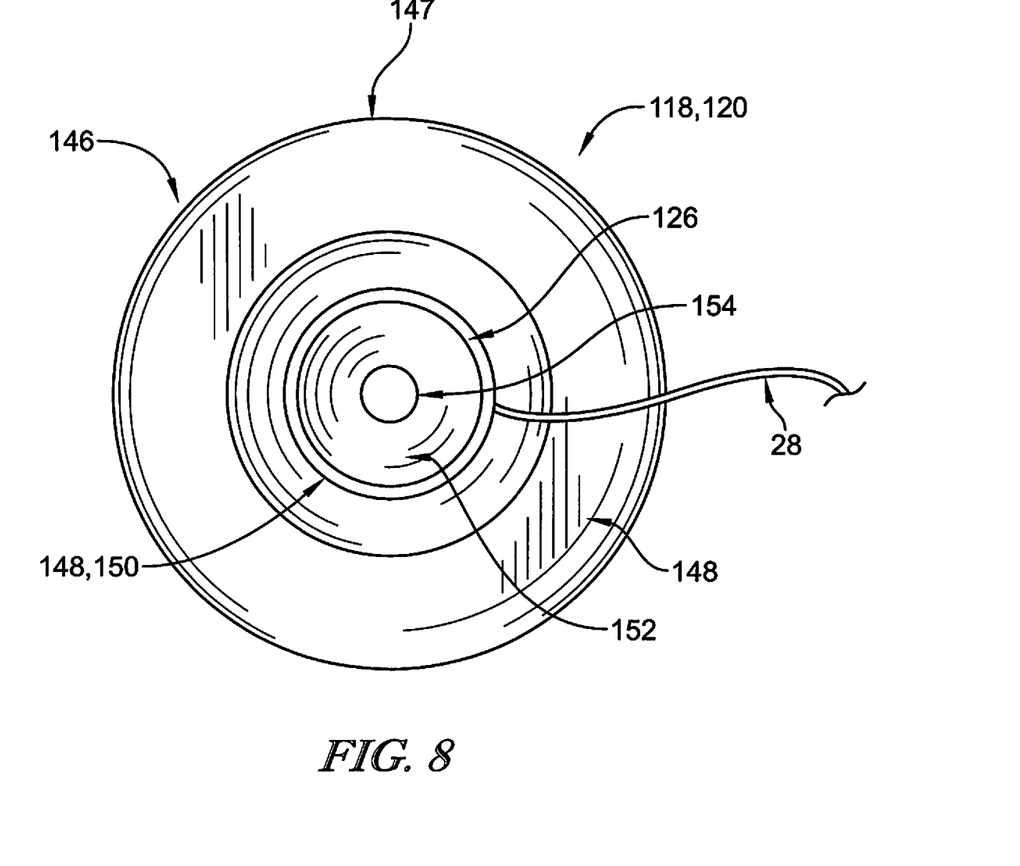
FIG. 8 is a top view of another illustrative embodiment of a pod of the electrostimulation system of FIGS. 1-4 showing that the pod includes a body having a contact area and a relief area, the relief area arranged within the contact area and having an opening defined therein, and a stimulator arranged within the relief area about the opening for providing electric polarity for conductance through the body.

As shown in FIG. 8, another illustrative embodiment of the pods 118, 120 is shown. Pods 118, 120 are illustratively similar to pods 18, 20 and the description above applies to pods 118, 120 except in instances where it conflicts with the specific description and illustration of pods 118, 120. Each pod 118, 120 illustratively includes a body 146 including a contact area 148 and a relief area 150 arranged within the contact area 148. The stimulation terminal 26 is illustratively arranged within the relief area 150. Unlike the pods 18, 20, the relief area 150 illustratively includes an opening 154 to relieve contact from the patient's body, and the stimulation terminal 126 is embodied as a ring member disposed about the opening 154. In some embodiments, the stimulation terminals 26, 126 may have any suitable shape, arrangement, and/or other form. The body 146 is illustratively formed as a circular disc but in some embodiments may be square or have any other suitable shape for engagement with the patient's body. The body 146 engages the patient's body, illustratively by direct adhesion to the skin, such that the casing 147 is in contact with the patient's skin to conduct voltage through the gel 145.

Figure 9:
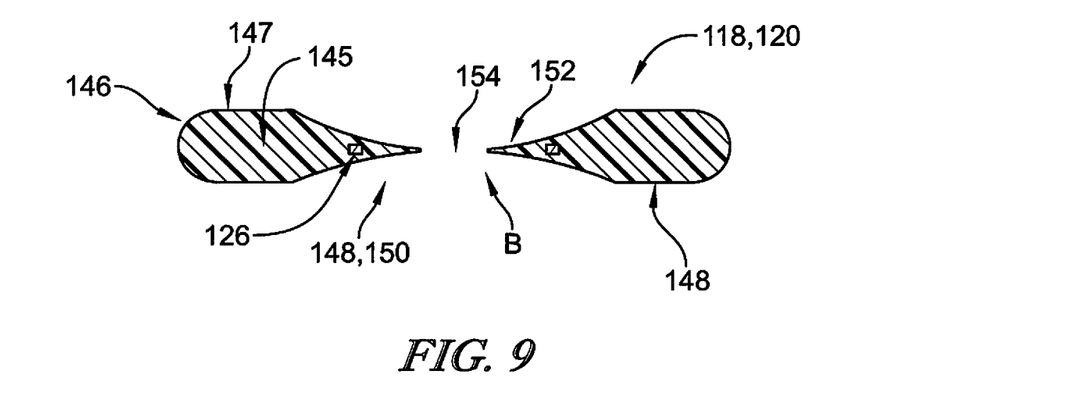
FIG. 9 is a side view of the pod of FIG. 8 showing that the contact area has a thickness, and the relief area has a transition thickness that forms a concave depression having the opening defined at an apex thereof to relieve loading to the patient's body.

As shown in FIG. 9, the relief area 150 is illustratively has a tapered thickness to form a depression 152. The stimulation terminal 126 is arranged about the opening 154 within the depression 152. The taper of the relief area 150 reduces loading to the area B at which the stimulation terminal 126 is applied and distributes forces to surrounding areas. This provides a low loading point at the engagement of the pod 118, 120 with the patient's body.

The present disclosure includes arrangements of electrodes 26, 126 placed in arrays of two or more on a patient's body to provide electrostimulation. For example but without limitation, an electrode 26, 126 can be placed on the posterior aspect of the body with a positive voltage and another electrode 26, 126 may be placed on the anterior aspect of the body with a positive voltage. The interaction of the electrodes 26, 126 can generate an electric field in the direction from the posterior electrode 26, 126 to the anterior electrode 26, 126. As more than two electrodes 26, 126 can be applied, the net electric field can be generated to have a range of directions based on the specific configuration of electrodes 26, 126 and their voltages.

The present disclosure includes pods 18, 20, 118, 120 formed as thinned disks and/or pads wherein the center of the pad is thinner than the outer areas so that contact pressure is distributed radially away from the high-pressure central area.

The present disclosure includes measurement of perfusion levels which may be measured by several means, for example but without limitation, from relative levels of optical absorption at different wavelengths or by measuring the amplitude change of the reference signal. Generally, reference to perfusion level may indicate a direct measure of the perfusion and/or a measure of a physical parameter such as the amplitude change of the reference signal that correlates to the perfusion level. In some embodiments, topical analgesics may be applied to numb cutaneous nerves, improve readings from deep nerves (and therefore blood flow/ischemia), and/or to direct electrical flow away from the cutaneous nerves (if for example, the two electrodes are in close proximity to one another).

The present disclosure includes use of the electrostimulation system 16 alone and/or with patient support devices including but not limited to beds, lifts, operating tables, stretchers, backboards, chairs, and the like.

Although certain illustrative embodiments have been described in detail above, variations and modifications exist within the scope and spirit of this disclosure as described and as defined in the following claims.

What is claimed is:

1. An electrostimulation system for encouraging perfusion in a patient's body, the system comprising:
   a number of first stimulation pods providing a first polarity, each first stimulation pod engaging the patient's body,
   a number of second stimulation pods providing a second polarity, each second stimulation pod engaging the patient's body and being arranged with proximity to the first stimulation pods to create a directed electric field to encourage perfusion in nearby areas of the patient's body, and
   a controller connected with each of the first and second stimulation pods to communicate at least one stimulation signal to produce the first and second polarities, respectively.

2. The electrostimulation system of claim 1, further comprising at least one sensor in communication with the controller, the sensor being adapted to indicate a measured perfusion level within the patient's body.

3. The electrostimulation system of claim 2, wherein the controller is configured to determine whether the measured perfusion level meets a threshold perfusion level.

4. The electrostimulation system of claim 3, wherein the controller is configured to determine updated parameters for at least one of the first and second stimulation pods in response to determination that the measured perfusion level does not meet the threshold perfusion level.

5. The electrostimulation system of claim 4, wherein the updated parameters include change in a stimulus value of at least one of amplitude, duty cycle, modulation, phase, and pulse frequency.

6. The electrostimulation system of claim 2, wherein the controller is configured to determine the measured perfusion level by sending a reference signal through the patient's body to produce at least one response, detecting the at least one response produced by the reference signal, and evaluating the at least one response to determine the measured perfusion level.

7. The electrostimulation system of claim 6, wherein the response includes an indication of reduced blood flow within a localized area of the patient's body.

8. The electrostimulation system of claim 6, wherein the response includes change of the reference signal passed through the patient's body.

9. The electrostimulation system of claim 6, wherein the response includes localized motion of the patient's body and the sensor includes a micro-motion sensor for detecting the motion of the patient's body.

10. The electrostimulation system of claim 2, wherein the controller is configured to determine a location of low perfusion of the patient's body based on the measured perfusion level.

11. The electrostimulation system of claim 10, wherein the controller is configured to determine a target direction of the directed electric field required to pass through the location of low perfusion and to adjust the at least one stimulation signal to achieve the directed electric field having the target direction.

12. The electrostimulation system of claim 11, wherein the controller is configured to determine that the target direction of the directed electric field required to pass through the location is beyond a capacity of the system according to current arrangement of first and second stimulation pods and to determine an adjusted arrangement of first and second stimulation pods to pass the directed electric field through the location.

13. The electrostimulation system of claim 12, wherein the controller outputs the adjusted arrangement of first and second stimulation pods onto a display for communication to a user.

14. A patient support system with electrostimulation for encouraging perfusion in a patient's body, the system comprising:
    a support surface including a number of first stimulation pods arranged to engage a body of a patient occupying the support surface, each first stimulation pod having a first polarity, and
    a number of second stimulation pods providing a second polarity, each second stimulation pod engaging the patient's body and being arranged with proximity to the first stimulation pods to create a directed electric field to encourage perfusion in nearby areas of the patient's body.

15. The patient support system of claim 14, further comprising a controller connected with each of the first and second stimulation pods to communicate at least one stimulation signal to produce the first and second polarities, respectively.

16. The patient support system of claim 15, further comprising at least one sensor in communication with the controller, the sensor being adapted to indicate a measured perfusion level within the patient's body.

17. The patient support system of claim 16, wherein the controller is configured to determine a location of low perfusion of the patient's body based on the measured perfusion level.

18. The patient support system of claim 17, wherein the controller is configured to determine a target direction of the directed electric field required to pass through the location of low perfusion and to adjust the at least stimulation signal to achieve the directed electric field to have the target direction.

19. The patient support system of claim 18, wherein the controller is configured to determine that the target direction of the directed electric field required to pass through the location is beyond a capacity of the system according to current arrangement of first and second stimulation pods and to determine an adjusted arrangement of first and second stimulation pods to pass the directed electric field through the location.

20. The patient support system of claim 19, wherein the controller outputs the adjusted arrangement of first and second stimulation pods onto a display for communication to a user.

* * * * *